US006540915B2

(12) United States Patent
Patil

(10) Patent No.: US 6,540,915 B2
(45) Date of Patent: Apr. 1, 2003

(54) ANTIMICROBIAL SEMI-PERMEABLE MEMBRANES

(75) Inventor: Arvind S. Patil, Davidson, NC (US)

(73) Assignee: Microban Products Company, Huntersville, NC (US)

(*) Notice: Subject to any disclaimer, the term of this patent is extended or adjusted under 35 U.S.C. 154(b) by 0 days.

(21) Appl. No.: 09/847,576

(22) Filed: May 2, 2001

(65) Prior Publication Data

US 2003/0038074 A1 Feb. 27, 2003

Related U.S. Application Data

(63) Continuation-in-part of application No. 09/342,779, filed on Jun. 29, 1999, now abandoned.
(60) Provisional application No. 60/090,996, filed on Jun. 29, 1998.

(51) Int. Cl.[7] .......................... B01D 71/00; B01D 39/00
(52) U.S. Cl. .......................... 210/500.27; 210/500.29; 210/500.28; 210/500.36; 210/500.38; 210/500.41; 210/500.42; 210/500.23; 210/484
(58) Field of Search .................. 210/500.38, 500.1, 210/500.41, 500.23, 497.1, 321.74, 484, 195.2, 500.27, 500.36, 500.42, 500.28, 500.29; 424/406, 78.01, 411; 428/461; 264/41

(56) References Cited

U.S. PATENT DOCUMENTS

| 3,417,870 A | 12/1968 | Bray .......................... 210/321 |
| 3,691,068 A | 9/1972 | Cross |
| 3,884,801 A | 5/1975 | Kesting |
| 4,500,517 A | 2/1985 | Luss .......................... 424/162 |
| 4,828,700 A | 5/1989 | Fibiger .................. 210/500.32 |
| 4,888,116 A | 12/1989 | Cadotte ...................... 210/636 |
| 4,894,165 A | 1/1990 | Fibiger ........................ 210/654 |
| 4,909,943 A | 3/1990 | Fibiger ........................ 210/654 |
| 4,913,816 A | 4/1990 | Waite ......................... 210/490 |
| 5,006,267 A | 4/1991 | Vaughn ....................... 210/755 |
| 5,028,337 A | 7/1991 | Linder ........................ 210/642 |
| 5,102,547 A | 4/1992 | Waite ......................... 210/501 |
| 5,102,898 A | 4/1992 | Hsu ........................... 514/375 |
| 5,169,712 A | 12/1992 | Tapp ....................... 428/315.5 |
| 5,229,172 A | 7/1993 | Cahalan ...................... 427/536 |
| 5,584,997 A | 12/1996 | Yagihashi .............. 210/321.79 |
| 5,762,797 A | 6/1998 | Patrick .................... 210/497.1 |
| 5,817,325 A | * 10/1998 | Sawan et al. |
| 5,868,933 A | * 2/1999 | Patrick et al. |
| 5,869,073 A | * 2/1999 | Sawan et al. |
| 6,126,931 A | * 10/2000 | Sawan et al. |
| 6,267,782 B1 | * 7/2001 | Ogle et al. |

FOREIGN PATENT DOCUMENTS

JP          01274814       * 11/1989

* cited by examiner

Primary Examiner—Ana Fortuna
(74) Attorney, Agent, or Firm—Dougherty, Clements & Hofer

(57) ABSTRACT

Cast semi-permeable membranes made from synthetic polymer used in reverse osmosis, ultrafiltration and microfiltration are treated with a non-leaching antimicrobial agent to prevent its bio-fouling and bacterial breakthrough. The semi-permeable membranes include a polymeric material and a non-leaching antimicrobial agent that is incorporated into and homogeneously distributed throughout the polymeric material. The polymeric material, in the case of one membrane, may be cellulose acetate. In the case of thin film composite polyamide membranes, the antimicrobial agent is incorporated in a microporous polysulfone layer that is sandwiched between a reinforcing fabric and an ultrathin polyamide material. The invention also includes a treatment of flat and hollow fiber semipermeable membranes made with polysulfones and polyvinylidene fluoride.

17 Claims, 4 Drawing Sheets

# ANTIMICROBIAL SEMI-PERMEABLE MEMBRANES

CROSS REFERENCE TO RELATED APPLICATION

This is a Continuation-In-Part of U.S. patent application Ser. No. 09/342,779 filed Jun. 29, 1999, now abandoned and this application claims the benefit of U.S. Provisional Application No. 60/090,996 filed Jun. 29, 1998.

FIELD OF THE INVENTION

This invention relates generally to filters for the purification of liquids. In particular, the present invention relates to antimicrobial semi-permeable cast membranes such as cellulose acetate or composite polyamide, polysulfone and polyvinylidine fluoride membranes used in reverse osmosis, ultrafiltration/nanofiltration and microfiltration.

BACKGROUND OF THE INVENTION

In recent years, the public has become increasingly aware of the deteriorating quality and quantity of our nation's and the world's fresh water supply. Pollutants, biological and toxic waste and other contaminants are being introduced into water supplies at an ever increasing rate, making such water supplies unfit for drinking and other necessary uses. For example, medical patients with low immunity are now being requested not to drink tap water, and disease and illnesses linked to poor quality drinking water have increased dramatically in recent years. This problem is especially significant outside of the United States where water quality has deteriorated to an all time low, with the major source of such contamination primarily being bacterial in nature.

In many areas of the world, potable water is not only contaminated but also scarce. In these areas, people must rely upon expensive purification systems to remove dissolved solids from seawater, brackish water, or well water. Reverse osmosis filtration systems are one of the most common solutions for improving water quality. Osmosis is the flow or diffusion that takes place through a semi-permeable membrane, such as in a living cell. The membrane typically separates either a solvent, such as water, from a solution, or a dilute solution from a concentrated solution. This membrane separation brings about conditions for equalizing the concentrations of the components on the two sides of the membrane because of the unequal rates of passage in the two directions until equilibrium is reached.

In reverse osmosis, pressure is deliberately applied to the more concentrated solution to cause the flow of solvent in the opposite direction through the membrane, for example, into the more dilute solution. In this way, the liquid can be separated from dissolved solids and thus increase the concentration of the dissolved solids in solution. Typically, the osmotic pressure of a solution containing 1000 ppm of dissolved salts is 10 psig. Most residential reverse osmosis units operate at less than 150 psig. Reverse osmosis units treating brackish waters operate at 150 to 450 psig, while those for seawater operate at 800 to 1000 psig.

The widespread use of reverse osmosis to produce potable water began in the early 1960's when Loeb and Sourirajan developed a cast thin-skin cellulose acetate membranes for use in reverse osmosis systems. These cellulose acetate membranes provided much higher salt rejection (approaching 95%) and solvent flow than previously known reverse osmosis methods. Cellulose acetate membranes are also relatively inexpensive and are very tolerant of chlorine, which is commonly used to eliminate bacteria in water. Since the 1960's, the use of reverse osmosis has grown dramatically in waste water applications and industrial desalinization plants to produce drinking water from brackish and sea waters. More recently, cast cellulose acetate membranes have been incorporated into consumer filtration systems to produce drinking water at the point of use. (Matsuura, T., Synthetic Membranes and Membrane Separation Processes, CRC Press, (1994)). Although cellulose acetate membranes greatly expanded the utilization of reverse osmosis treatment systems, such systems are still restricted by operational problems. For example, cellulose acetate membranes hydrolyze and biodegrade readily. Therefore, a need exists for alternative membranes for use in reverse osmosis systems.

Recently, a cast thin film composite polyamide membranes have been developed that offer better performance than cellulose acetate membranes. (See for example, U.S. Pat. Nos. 4,277,344, 4,520,044 and 4,606,943). Composite polyamide membranes have a bottom layer of reinforcing fabric usually made of polyester, on top of which is typically deposited a layer of polysulfone polymer. The layer of polysulfone polymer is typically 40 microns thick. A 0.2-micron ultrathin layer of polyamide is then cast on the top of the polysulfone layer. (Singh, R., "Membranes", Ultrapure Water, March 1997). The porous polysulfone support is saturated with water-soluble amine solution, and acid chloride solution is then applied to bring about an in situ polymerization to the polyamide. For example, U.S. Pat. No. 3,551,331 describes a process for modifying the permeability of linear aliphatic polyamide membrane.

The polyamide layer enables the composite polyamide membrane to exhibit salt rejection rates greater than 99.5% at pressures much lower than the pressures used for cellulose acetate membranes. Additionally, polyamide membranes reject silica, nitrates, and organic materials much better than cellulose acetate membranes. Because of the high performance of composite polyamide membranes, these membranes are used in high purity or ultrahigh purity water systems in pharmaceutical and electronics industries. However, just as cellulose acetate membranes exhibit a limiting characteristic, for example, biodegradation, so do composite polyamide membranes. Composite polyamide membranes are also susceptible to damage from chlorine. To overcome some of these shortcomings, other types of cast membranes have been developed that use different types of polymers.

As the technology for manufacturing composite polyamide, cellulose acetate and other types of membranes has progressed, new fields of filtration, such as ultrafiltration, or nanofiltration, and microfiltration have been created. Many of these membranes utilize a support layer having a relatively high degree of porosity followed by an ultra-thin layer of another polymeric coating, such as the polyamide layer described above, that allows for a high salt rejection or rejection of various ranges of molecular weights of organic substances. Additionally, the support membranes, or structures, are either woven or nonwoven and are typically made from polyolefins, polyester, aromatic polysulfones, polyphenylenesulfones, aromatic polyether sulfone, bisphenol A, dichlorodiphenoxysulfone, aromatic polyether ketones, sulfonated polyether ketones, phenoxides made from epichlorohydrin and bisphenol A, polyvinylidene fluoride or sulfonated polyvinylidene fluoride, nylon, vinyl chloride homo- and co-polymers, polystyrene, polytetrafluorethylene, glass fiber, porous carbon, graphite, inorganic membranes based on alumina, and/or silica with coating of zirconium oxide. The support structure is either in the form of a flat sheet or a hollow fiber configuration depending on the desired characteristic nature of the final membrane.

U.S. Pat. No. 5,028,337 ("'337") describes compositions of many types of cast membranes and methods of preparing the same. In particular, the '337 patent discloses an ultra-thin polymeric coating on a porous support which may be selected from the following polymers, which may be in turn halomethylated, quaternized and/or sulfonated, as desired or necessary prior to a coating step: aromatic oxide polymers, such as 2,6 dimethyl polyphenyleneoxides, aromatic polysulfones, aromatic polyethersulfones, aromatic polyether ketones, linear polyaromatic epoxides; aryl polymers, such as polystyrene and poly (vinyl toluene) polymers; and, sulfonated poly (haloalkylene) polymers, such as sulfonated polyvinyl chloride, polyvinyl fluoride, polyvinylidene fluoride or polyvinylidene fluoride/hexafluoropropylene.

Casting of polymeric membranes on the support structures described above that are made of polysulfones, polyether sulfones, polyether ketones, polyvinylidene fluoride, sulfonated polyvinylidene fluoride or polyacrylonitrile may be accomplished by any number of casting procedures extensively described in published patent and technical literature. (See, for example, U.S. Pat. Nos. 3,556,305; 3,567,810; 3,615,024; 4,029,582; and 4,188,354; GB 2,000,720; Office of Saline Water R & D Progress Report No. 357, October 1967; Reverse Osmosis and Synthetic Membranes, Ed. Sourirajan; Murari et al; J. Member Sci. 16:121–135 and 181–193 (1983)).

Typically, in the manufacture of cast membranes on a support structure, the polymer or its derivatives are dissolved in a suitable solvent, such as N-methyl-pyrollidone ("NMP"), di-methyl formamide ("DMF"), di-methyl sulfoxide, hexamethylphosphoramide, N,N-dimethylacetamide, and dioxane. Additionally, the polymer or its derivatives are dissolved in a solvent mixture of the aforementioned solvents with or without cosolvents, partial solvents, nonsolvents, salts, surfactants or electrolytes for altering or modifying the membrane porosity, flux and rejection properties, such as acetone, methanol, formamide, water, methyl ethyl ketone, triethyl phosphate, sulfuric acid, HCl, partial esters of fatty acids and sugar alcohol, or their ethylene oxide adducts, sodium dodecyl sulfate, sodium dodecylbenzene sulfonate, NaOH, KCl, zinc chloride, calcium chloride, lithium nitrates, LiCl, and magnesium perchlorate. The concentration of polymer in the casting solution is dependent on its molecular weight and also on the additives that may be present. The widest range of concentration may be between 5% to 80%, but more typically, the range of concentration is from 15% to 30%. The casting temperature may vary from −20° C., to 100° C. and is typically from 0° C. to 10° C.

The casting solution can be applied to porous supports by any conventional techniques that are familiar to those skilled in the art. The wet film thickness is typically between 100 to 500 microns for the flat membrane, but the broadest range may be between 15 micron to 5 mm. For hollow fibers or tubular forms, the thickness can be even higher. In order to control the porosity of the cast film, the wet film on the support may be immersed in a precipitating bath immediately or may be subjected to partial drying for 5 seconds to about 48 hours under ambient conditions or elevated temperatures, under atmospheric conditions or under vacuum. The precipitating bath is usually made up of water to which small amounts of solvent, such as DMF or NMP, and surfactant, such as sodium dodecyl sulfate, are added. The bath is usually maintained at a temperature of between 0° C. to 70° C. A typical precipitating bath is water with 0.5% sodium dodecyl sulfate at a temperature of 4° C.

Some membranes are formed with a polymer solution containing a component, which may be leached out in water or other solvent. The cast membrane is dried and then a subsequent immersion step removes the leachable material to result in the creation of porosity. Other membranes, such as cellulose acetate, are cast from a polymer solution without any leachable materials, dried and annealed by subjecting the material to heat or pressure to further modify the pore structure.

Another process for making membranes used for ultrafiltration and microfiltration involves extrusion and controlled thermostretching and cooling. Examples of materials used in such membranes include microporous polytetrafluoroethylene, polypropylene and polyethylene. Chemical compounds of various sizes and molecular weights are selectively filtered out by manipulating the pore sizes of these membranes. For example, membranes used in reverse osmosis, or hyperfiltration, remove particles of 1 to 10 Angstrom units and include chemical compounds of about 180 to 15,000 molecular weights. Ultrafiltration filters particles of 30 to 1100 Angstrom units that include macromolecules of molecular weight of 10,000 to 250,000. Microfiltration, which is mainly used to remove bacteria from a solution, filters in the range of 500 Angstroms to 20,000 Angstroms (0.05 to 2 micron) (Lonsdale, H. K. "The Growth of Membrane Technology" Journal of Membrane Science, 10, p.80–81 (1982)).

All of the membranes mentioned above can be in the form of a flat sheet or in a hollow fiber configuration with a bore in the center of each fiber. For example, U.S. Pat. No. 5,762,798 ("'798") describes a method of manufacturing a hollow fiber polysulfone membrane. Further, the membrane disclosed in the '798 patent may be either asymmetric or symmetric. Asymmetric membranes have pore sizes on one face of the membrane that are different from those pore sizes on the other face of the membrane. Typically, the narrower pores on one of the faces give way to the tortuous branchings of the larger pores that exit on the other face. Asymmetric membranes commonly have higher fluid flux. In comparison, symmetric membranes have pore sizes that are the same on either face and have no tortuosity of pore channels.

However, the ability to remove dissolved particles from water comes with a price. Bacteria contained in the influent water are arrested by the semi-permeable membranes and, consequently, accumulate on the surface of the membranes. Bacteria typically multiply every 30 to 60 minutes and their growth is logarithmic. For example, a single bacterial cell will result in 16 million bacteria in 24 hours. The explosive growth of bacteria results in fouling of the membrane which reduces the flow of water through the membrane and can adversely affect the filtering properties of the membrane. For example, bacteria build-up typically has an adverse affect on salt rejection in a reverse osmosis membrane. (Wes Byrne, Reverse Osmosis, Chapter 9—Biological Fouling).

Furthermore, fouled membranes require higher operating pressures, which in turn increases operating costs. Alternatively, cleaning of reverse osmosis membranes using chemicals requires 20% of the total operating time of a reverse osmosis facility, thereby resulting in a dramatic reduction in the overall efficiency of the process. (Ebrahim, S. "Cleaning and Regeneration of Membranes in Desalination and Waste Water Applications: State of the Art", Proceedings of the International Desalination Association and Water Use Promotion Center World Conference, vol. 1, pp. 197–208, Yokohama, Japan (Nov. 3–6, 1993)). Standard fouling factors for reverse osmosis, ultrafiltration and microfiltration membranes are 30%, 80% and 90%, respectively. Thus, the fouling rate is the most important consideration in designing a water treatment plant that utilizes a membrane process. (Denese Tracey, "Membrane Fouling", Ultrapure Water, October, 1996).

In addition to reducing water quality, fouled membranes are difficult to clean. As a result of the bacterial growth on the membrane, a gelatinous biofilm is formed on the upstream surface of the membrane, which is very difficult to remove, except through the use of strong chemical oxidants that damage the membrane. The biofilm protects the bacteria from normal cleaning and sanitizing procedures and leads to a break through of bacteria across the membrane. The bacterial penetration could also occur along defects in the membrane. Typically, bacteria are detected on the downstream side of the membrane within 48 to 72 hours. The downstream side of the membrane becomes noticeably discolored or black over time as the bacteria colonize on the downstream side of the membrane and form a biofilm. Such biological fouling can also lead to the formation of localized extremes in pH that can further damage the membrane. Thus, conventional semi-permeable filters standing alone rarely provide ultrapure (e.g. bacteria free) water. In many instances, reverse osmosis, ultrafiltration and microfiltration processes must be followed by polishing filters to clean the water of bacteria.

It should be pointed out that membranes can also be produced by processes of extrusion and thermostretching, but these suffer from the lack of homogeneity and unsuitable range of pores for this application.

What is therefore needed is a semi-permeable cast membrane filter that provides substantially ultrapure water. More particularly, a need exists for a semi-permeable membrane that may be used in reverse osmosis, ultrafiltration, nanofiltration and microfiltration to produce substantially ultrapure water without the assistance of additional filtering means. Further, a need exists for a filter membrane that resists fouling caused from bacterial growth.

OBJECTS OF THE INVENTION

The principal object of the present invention is to provide a cast semi-permeable membrane filter that provides substantially ultrapure water.

Another object of the present invention is to provide a cast semi-permeable membrane having an antimicrobial agent incorporated therein.

Another object of the present invention is to provide a cast filter membrane that achieves a high level of separation of water-soluble contaminants.

Another object of the present invention is to provide a cast membrane filter that resists fouling due to bacterial growth.

Another object of the present invention is to provide a cast membrane filter that inhibits the passage of bacteria to the downstream side of the membrane.

Another object of the present invention is to provide a cast membrane filter that reduces downtime for water treatment processes.

SUMMARY OF THE INVENTION

The present invention is a cast semi-permeable membrane filter that provides substantially ultrapure water. In particular, the present invention provides a semi-permeable membrane that may be used in reverse osmosis, ultrafiltration, nanofiltration and microfiltration to achieve a high level of separation of water soluble contaminants without the assistance of additional filtering means. The membrane comprises a non-leaching antimicrobial agent within the membrane structure.

In a most basic form, the invented cast semi-permeable membrane comprises a microporous layer of polymeric material and a non-leaching antimicrobial agent that is incorporated into the polymeric material of the microporous layer. The microporous layer may be in the form of a flat film or sheet or a hollow fiber configuration. A porous support layer, such as a reinforcing fabric, may be combined with the polymeric microporous layer that removes inorganic or bacterial contaminants. The support layer provides added mechanical strength to the semi-permeable membrane. Because of the exacting requirements with respect to pore sizes it has been found that only cast membranes are able to perform to eliminate dissolved inorganic and organic ions. No extruded membranes have been able to meet these exacting requirements so far.

In one embodiment of the present invention, the cast semi-permeable membrane comprises a thin film of cellulose acetate polymer, and the antimicrobial agent is dispersed homogeneously throughout the thin film of cellulose acetate. The antimicrobial agent is selected from the group consisting of 2,4,4'-trichloro-2'-hydroxy diphenol ether and 5-chloro-2-phenol (2,4-dichlorophenoxy). Preferably, the antimicrobial agent is present in a concentration between about 2,500 ppm and 20,000 ppm by weight based upon a total cellulose acetate polymer content of about 15 to1 8%.

In another embodiment of the claimed invention, the polymeric material of the cast semi-permeable membrane comprises a microporous polysulfone material having a thickness between about 20 microns and 60 microns and the antimicrobial agent dispersed homogeneously throughout the microporous polysulfone material. The antimicrobial agent is selected from the group consisting of 2,4,4'-trichloro-2'-hydroxy diphenol ether and 5-chloro-2-phenol (2,4-dichlorophenoxy). The antimicrobial agent is present in a concentration between about 50 ppm to 20,000 ppm by weight based upon a total polysulfone polymer content of about 15% to 18%. To form the membrane, a layer of microporous polysulfone material having a thickness of about 20 to 60 microns thick is deposited onto a reinforcing fabric that has a thickness between about 75 microns and 150 microns thick. An ultrathin layer of polyamide material between about 0.08 microns to 0.4 microns is then formed on the exposed surface of the polysulfone material by reaction of amine and acid chloride on the surface of the composite membrane in the presence of a catalyst.

In another embodiment of the present invention, the polymeric material of the cast semi-permeable membrane comprises a plurality of microporous hollow fibers made from polysulfones or polyvinylidene fluoride that incorporates the non-leaching antimicrobial agent. The antimicrobial agent is dispersed homogeneously throughout the microporous hollow fibers. These hollow fibers are preferably microporous polymeric capillary tubes having an outside diameter that is less than about 2 mm and a wall that functions as a semi-permeable membrane. The antimicrobial agent is selected from the group consisting of 2,4,4'-trichloro-2'-hydroxy diphenol ether and 5-chloro-2-phenol (2,4-dichlorophenoxy). The antimicrobial agent is present in a concentration between about 50 ppm to 20,000 ppm by weight based upon the weight of the polysulfone and polyvinylidene fluoride polymer. A wide variety of hollow fiber membranes are made depending on desired applications, including but not limited to reverse osmosis, ultrafiltration, and microfiltration.

DETAILED DESCRIPTION OF THE INVENTION

Figure 1:
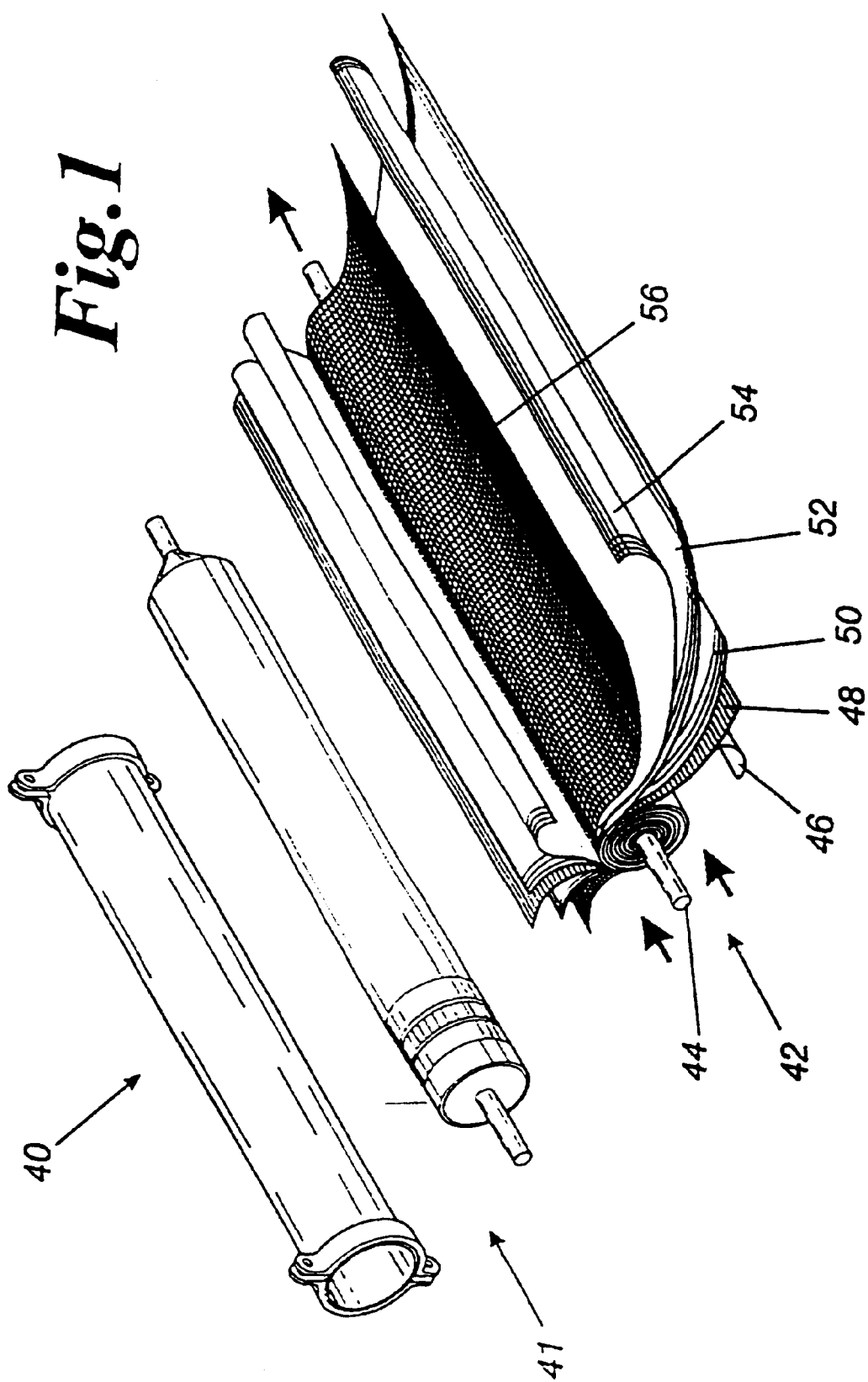
FIG. 1 is an exploded view of a reverse osmosis module in accordance with the present invention, showing the module housing and the spiral filter.

As used herein, terms such as "front", "rear", "side", "up", and "down" are used for purposes of locating one element of the present invention relative to another and are not intended to be construed as limiting terms. Further, the illustrations are for the purpose of describing preferred embodiments of the invention, and thus are not intended to limit the invention in any manner. The term "incorporated" as used in relation to the non-leaching antimicrobial agent is defined herein to mean substantially residing in the interstices of the polymeric matrix of the polymeric material.

The present invention is particularly suited to create both cellulose acetate, composite polyamide, polysulfone, and polyvinylidene fluoride type reverse osmosis membranes that prevent the growth of bacteria on the membrane as well as the break through of bacteria across membrane. Such membranes are created by incorporating non-leaching antimicrobial additive, such as 2,4,4'-trichloro-2'-hydroxy diphenol ether or 5-chloro-2-phenol (2,4-dichlorophenoxy), commonly sold under the trademark MICROBAN® Additive B by Microban Products Company of Huntersville, N.C. Incorporation of the antimicrobial additive into the invented membrane does not affect the filtering properties of the invented membranes, yet prevents bacteria from forming biofilm on its surface or breaking through, or breaching, the membrane. More importantly, MICROBAN® Additive B, despite being very efficacious in preventing the growth of most kinds of bacteria encountered in water, does not leach out of the membrane and is safe, non-toxic, non-carcinogenic, non-sensitizing to human and animal skin and does not accumulate in the human body when ingested.

In a most basic form, the present invention is a membrane system comprising at least one cast semi-permeable membrane having a polymeric material and a non-leaching antimicrobial agent incorporated in the polymeric material and dispersed throughout said polymeric material. The polymeric material is selected from the group consisting of cellulose acetate polymer, polyacrylonitriles, polyester, aromatic polysulfones, polyphenylenesulfones, aromatic polyether sulfone, bisphenol, dichlorophenoxy sulfones, polyether ketones, sulfonated polyether ketones, phenoxides, polyvinylidene fluoride, nylon, vinyl chloride, polystyrene, and polytetrafluoroethylene.

The non-leaching antimicrobial agent is a chlorinated phenol and preferably selected from the group consisting of 2,4,4'-trichloro-2'hydroxy diphenol ether or 5-chloro-2 phenol (2,4-dichlorophenoxy). The concentration of the antimicrobial agent is between 100 ppm and 20,000 ppm by weight. Once the antimicrobial agent is incorporated into the polymeric material of the semi-permeable membrane, the antimicrobial agent does not leach out of the membrane. The semi-permeable membrane may optionally be a thin film composite membrane in which the polymeric material, having the non-leaching antimicrobial agent incorporate therein, is interposed between a reinforcing fabric and a polyamide layer.

The semi-permeable membrane, having the non-leaching antimicrobial agent incorporated therein, may be used in a reverse osmosis module. In one embodiment, the module comprises a perforated core, a spiral filter, an outer wrap substantially enclosing the spiral filter, and a housing containing the core, the filter, and the outerwrap. The spiral filter comprises at least one layer of a filtering structure having at least one of the previously mentioned semi-permeable membranes. The filtering structure preferably comprises a first semi-permeable membrane, a first backing material supporting the first membrane, a second semi-permeable membrane, a second backing material supporting the second membrane, and a porous permeate carrier interposed between the first backing material and the second backing material. This filtering structure is wound about the perforated core and enclosed by the outerwrap.

As fluid is passed through one end of module, the fluid is filtered by the semi-permeable membrane layers of the spiral filter and permeate is collected by the permeate carrier. The permeate carrier transports the permeate to the perforated core. Concentrate exits the other end of the module and permeate is separately collected and transported by the perforated core.

In another embodiment, the reverse osmosis module comprises a bundle of semi-permeable membranes in the form of thin hollow polymer fibers, a layer of epoxy resin for securing the ends of the polymer fibers, a porous disk positioned adjacent the epoxy resin, and a housing for substantially enclosing the hollow polymer fibers, the epoxy resin, and the porous disk. The polymer fibers are closed at one end and open at the other end. The open end is in fluid contact with the porous disk. Fluid is passed into the module through a feed inlet of the housing, and permeate is collected by the hollow polymer fibers and transported to the porous disk. The porous disk is in fluid contact with a permeate outlet of the housing. The housing additionally has an opening for the disposal of concentrate solution that contains the dissolved inorganic salts.

Cellulose Acetate Membranes

In one embodiment of the present invention, a cast cellulose acetate membrane is made by dissolving cellulose diacetate and cellulose triacetate in a solvent mixture where dioxane is the solvent. In addition, acetone, which has a boiling point at least 40° C. lower than the solvent, is used as a pore forming liquid. Methanol and maleic acid are used as swelling agents in the formation of the cellulose acetate membrane. The composite solution is commonly known in the art as "dope".

The antimicrobial agent is readily soluble in the solvent mixture, preferably comprising acetone and dioxane, that is used to dissolve the cellulose acetate. Higher acetate content has been found to improve salt rejection. Cellulose acetate and cellulose triacetate are preferably used as a mixture in a ratio of about 2:1 to 1:1. The dope solution preferably has a total cellulose acetate and triacetate solids of about 10 to 20%. The amount of antimicrobial agent that is added to the dope solution is based on the total solids content of the dope solution and is preferably within the concentration range of about 100 ppm to 20,000 ppm. More preferably, the concentration range of added antimicrobial agent is from about 5000 ppm to 15,000 ppm.

The dope is cast on a moving belt, either alone or on a support fabric made from either polyester or polypropylene, and allowed to precipitate at a temperature of about 5° C. to 10° C., into a film that is between about 50 to 500 microns thick. The antimicrobial agent precipitates along with the acetate polymer to produce a homogeneous distribution of antimicrobial agent in the resultant cellulose acetate membrane. After casting, the membrane is allowed to dry for about 1 to 3 minutes. This partially dried membrane is then immersed in water at 0° C. to 5° C. and the solvent mixture is removed to form a primary gel structure. The washed membrane is then annealed at 70° C. to 90° C. Annealing to progressively higher temperature results in a membrane that has increased density, decreased pore diameter and increased salt rejection. After optimum annealing, the membrane has about 90 to 95% salt rejection. An example of how an antimicrobial cellulose acetate membrane is formed is set forth in Example 1, hereinbelow.

Hollow Fiber Membrane

In another embodiment of the present invention, hollow fiber membranes are made from polysulfones, polyether sulfones, polyether ketones, polyvinylidene fluoride, sulfonated polyvinylidene fluoride or polyacrilonitrile. The dope solution for the aforementioned polymers, either singly or in combination with hydrophilic polymers such as polyvinylpyrrolidone, is made in polar aprotic solvents such as dimethylforamide (DMF), dimethylsulfoxide (DMSO), dimethylacetamide (DMA), n-methylpyrrolidone (NMP) and mixtures thereof.

Figure 2:
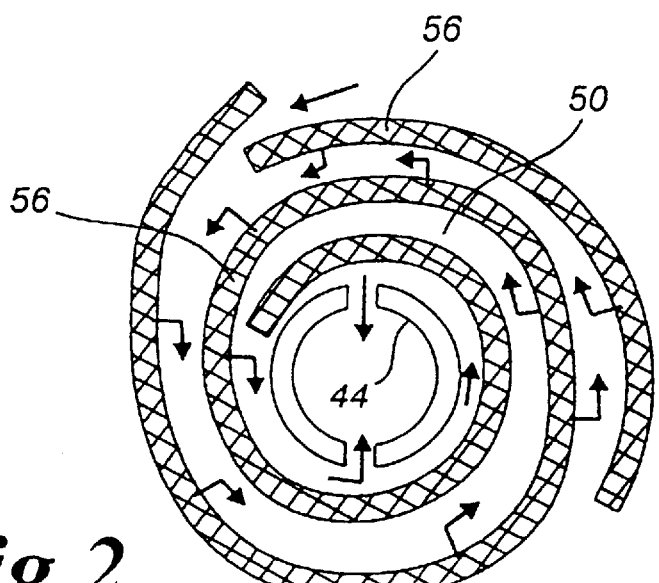
FIG. 2 is a cross sectional view of the spiral filter of FIG. 1, showing the flow of permeate.
Figure 3:
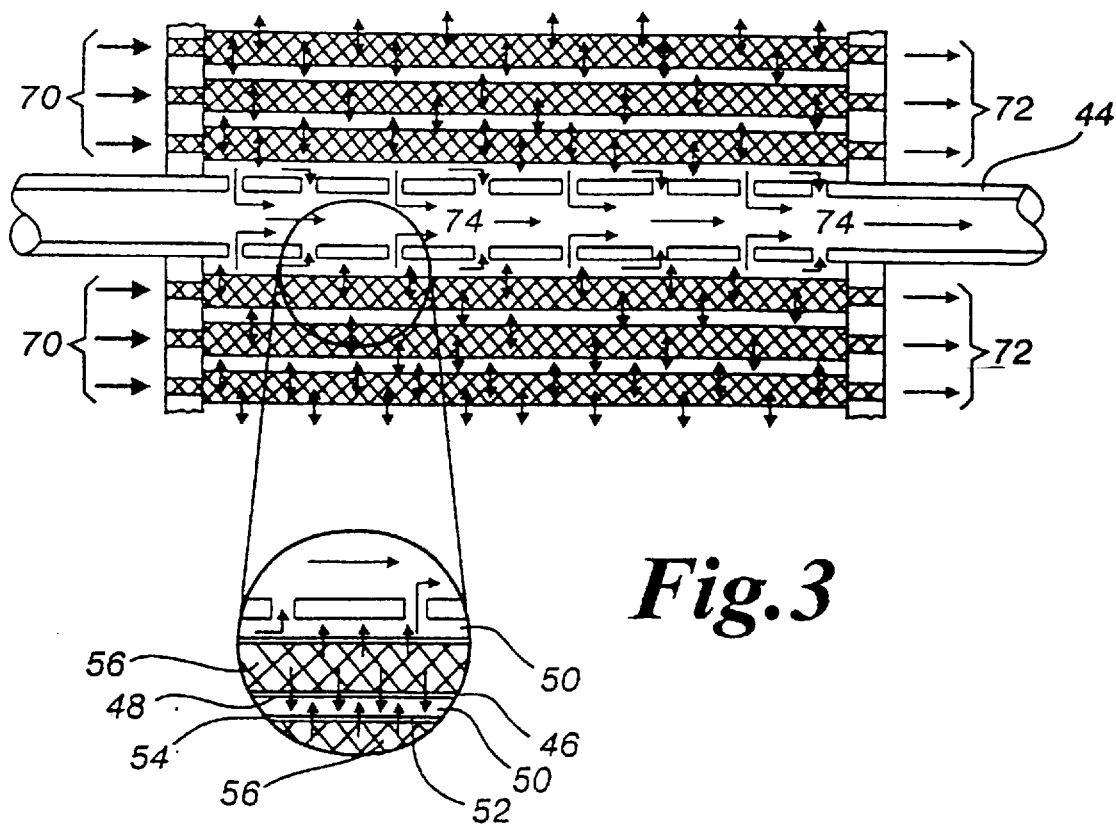
FIG. 3 is a partial longitudinal sectional view of the spiral filter of FIG. 1, showing the flow of permeate.

The antimicrobial agent is selected from a group of antimicrobial agents that are readily soluble in the aforementioned aprotic solvents yet will precipitate out along with the polymer in a precipitating step when a non-solvent comes into contact with the dope solution. Preferably, the antimicrobial agent is selected from the group consisting of 2,4,4-trichloro-2-hydroxy diphenol ether and 5-chloro-2-phenol (2,4-dichlorophenoxy), commonly sold under the trademark MICROBAN® Additive B by Microban Products Company of Huntersville, N.C. The typical concentration of antimicrobial agent in the dope solution is between about 100 to 10,000 ppm based on the total solids in the dope. The range of concentration of antimicrobial agent is preferably between 2500 to 10,000 ppm. The antimicrobial agent is added to the dope solution. Because the antimicrobial agent is readily soluble, the antimicrobial agent forms a homogeneous mixture with the aforementioned polymers. The hollow fibers are cast by a solution spinning process by passing the dope solution through a spinneret where the dope solution contacts a precipitating solution to form the hollow fiber. The precipitating solution is made of an aprotic solvent mixed with a pre-determined amount of non-solvent, such as water. An example of a spinneret assembly that can be used for the present invention is shown in FIGS. 2 and 3 of U.S. Pat. No. 5,762,798.

Alternatively, a hollow polyester support tube of about 0.5 to 2 mm in diameter may be used to form hollow fiber membranes. The support tube is passed through the dope solution having a pre-determined viscosity to form a film on the support tube. The formed film is subsequently contacted with the precipitating solution to form the hollow fiber membrane. An example of a manufacturing apparatus that may be used for this type of supported hollow fiber membrane manufacturing is shown in FIG. 1 of U.S. Pat. No. 5,762,798.

Composite Polyamide Membrane

In another embodiment of the present invention, a cast composite polyamide membrane is formed in a manner similar to the previously mentioned cellulose acetate membrane. A dope solution of polysulfone and antimicrobial agent is prepared and then cast in a thin layer onto a reinforcing fabric. The reinforcing fabric is preferably a polyester fabric between about 80 microns and 160 microns thick. Although polyester fabric is a preferred reinforcing fabric, other conventional reinforcing fabrics may be used in place of the polyester fabric. The casting of the dope solution onto the reinforcing fabric is accomplished in the following manner. First, the reinforcing fabric is carried by a moving belt that is initially immersed in water. Second, the dope solution is deposited onto the moving reinforcing fabric behind a doctoring blade. As the fabric travels under the doctoring blade, a thin film of dope solution is formed on the reinforcing fabric. The position of the doctoring blade controls the thickness of the polysulfone layer. The polysulfone layer is preferably deposited with a thickness of about 20 microns to about 60 microns. The wet supported film may be immersed immediately in a gelling bath of nonsolvents. Alternatively, the film may be immersed in the gelling bath after a partial drying step of about 5 seconds to 48 hrs under ambient temperature, elevated temperature, or under vacuum. Such gelling baths generally are water with a small percentage of solvents, such as DMF and NMP. The gelling bath is preferably maintained at 4° C.

When the dope solution contacts the water, the polysulfone and the antimicrobial agent precipitate onto the polyester reinforcing fabric to form a film. Based on the composition of the dope solution, the addition of consolvents, nonsolvents, electrolyte, and surfactants, the rate at which the precipitation of the polysulfone occurs, and subsequent temperature treatment, the pore size of the resulting membrane is determined. The polysulfone membrane is then dried and wound on a roll. In a separate process step, the polysulfone membrane is soaked with an amine solution and placed on a moving belt in a kerosene bath comprising an organic peroxide catalyst, such as t-butyl hydroperoxide. The amine absorbed in the polysulfone membrane is thus converted to an amide to form a polyamide layer on the polysulfone membrane with a thickness of about 0.2 microns. The resulting polyamide composite membrane is then dried and ready for use as a reverse osmosis membrane.

EXAMPLES

Example 1

Four cellulose acetate membranes were formed from a dope solution comprising the following constituents:

Weight Percentage

| | |
|---|---|
| 51.1% | Dioxane |
| 20.4% | Acetone |

-continued

| | |
|---|---|
| 10.8% | Cellulose Diacetate |
| 7.2% | Cellulose Triacetate |
| 7.8% | Methanol |
| 2.7% | Maleic Acid |

The above dope solution contains about 18% cellulose polymer solids. The four cellulose acetate membranes were cast with MICROBAN® Additive B concentrations at 2,500, 5,000, 10,000 and 20,000 ppm by weight based upon the approximate total cellulose polymer content of about 18%.

The cast cellulose acetate membranes were analyzed for MICROBAN® Additive B using gas chromatography, the results of which are shown below in Table 1.

TABLE 1

| MICROBAN ® Additive B Content In Dope Solution (ppm of polymer solids) | MICROBAN ® Additive B Content In Cellulose Acetate Membrane (ppm) |
|---|---|
| 2,500 | 2,350 |
| 5,000 | 4,500 |
| 10,000 | 9,200 |
| 20,000 | 18,500 |

The test results shown in Table 1, confirm that at least 90% of the antimicrobial agent was precipitated with acetate polymers and was retained in the polymeric material of the cellulose acetate membranes.

The four cellulose acetate membranes were tested in a Kirby Bauer Test. A portion of each membrane was placed on inoculated petri dishes of Gram positive Staphylococcus aureus and Gram negative Klebsiella pneumoniae, incubated for 24 hours, and observed for zones of inhibition around the samples. The results of the Kirby Bauer testing on the cellulose acetate membranes are shown below in Table 2. The test results shown in Table 2 indicate that the membranes exhibited good zones of inhibition at MICROBAN® Additive B levels between about 5,000 and 10,000 ppm.

TABLE 2

| Membrane Samples with Microban Concentration | Zone of Inhibition S. aureus | Zone of Inhibition K. pneumoniae |
|---|---|---|
| 2172–2500 ppm | 1 mm | 2 mm |
| 2173–5000 ppm | 5 mm | 5 mm |
| 2174–10,000 ppm | 7 mm | 9 mm |
| 2175–20,000 ppm | 9 mm | 10 mm |

The cellulose acetate membranes were then used to form a reverse osmosis module shown generally at 40 (FIG. 1). FIG. 1 is an exploded view of the reverse osmosis module 40 in accordance with the present invention showing a module housing, shown generally at 41, and a spiral filter, shown generally at 42. The reverse osmosis module 40 houses a spiral filter 42 comprising a hollow perforated core 44 about which is wound at least one layer of cellulose acetate membranes and spacing material. The cellulose acetate membranes and spacing material are arranged to form the multi-layered filter 42. The filter 42 comprises an acetate membrane 46 that is supported by a backing 48 which is adhesively attached to a porous permeate carrier 50. The carrier 50 is adhesively attached to a second backing 52 that supports a second acetate membrane 54. A mesh spacer 56 is then placed over the second acetate membrane 54 as the multi-layered filter is wound about the hollow perforated core 44.

FIG. 2 is a cross sectional view of the multi-layered filter and the core of FIG. 1, showing the path of permeate through the multi-layered filter 42. FIG. 3 is a sectional view of the multi-layered filter and the core of FIG. 1, showing the path of permeate through the multi-layered filter 42. When unfiltered fluid 70 is fed through the multi-layered, or spiral, filter 42, permeate 74 is transported by the permeate carrier 50 to the core 44 and concentrate 72 is transported through the reverse osmosis module 40 by the spiral filter 42. The reverse osmosis module 40 was tested to determine any bacterial presence in the permeate. After one month of operation no bacterial break through of the membrane was observed as determined by a standard microbiological plate count. The cellulose acetate membranes also exhibited a salt rejection of greater than 95%.

Example 2

Figure 4:
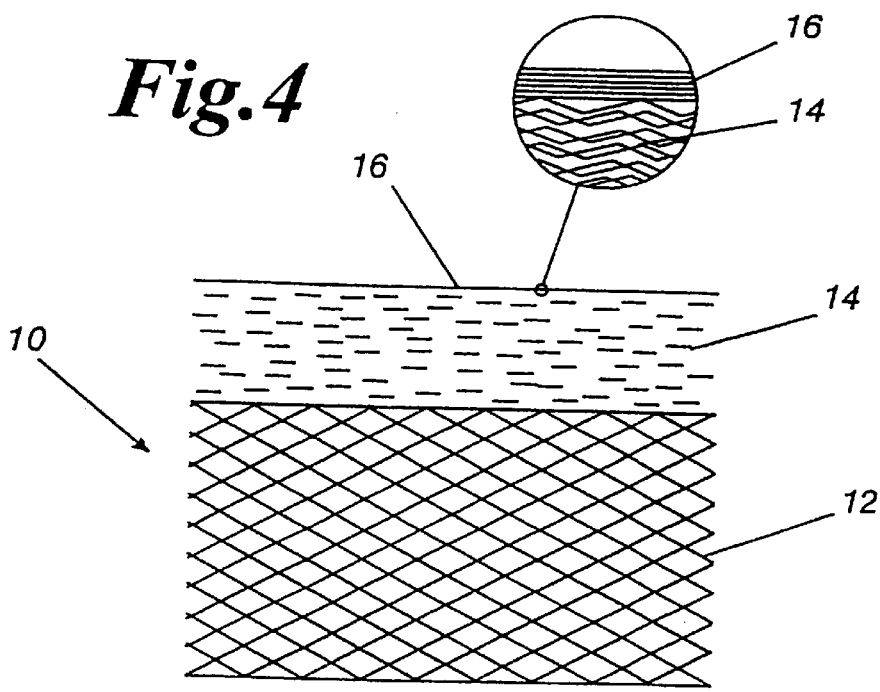
FIG. 4 is a schematic sectional view of a thin film composite polyamide reverse osmosis membrane in accordance with the present invention.

FIG. 4 is a schematic cross section of a thin-film composite polyamide reverse osmosis membrane, shown generally at membrane 10, in accordance with the present invention. To form the composite polyamide reverse osmosis membrane 10, a dope solution of polysulfone was prepared in dimethyl formamide (DMF) solvent. The polysulfone used was sold under the trade name "U.C.P. 1700" by Union Carbide. The dope solution contains about 18% polysulfone by weight and MICROBAN® Additive B of about 2% of the weight of the polysulfone. The dope solution was then deposited onto a reinforcing fabric of polyester 12 that was approximately 120 microns thick. A precipitating bath containing water and about 0.5% sodium dodecyl sulfate was maintained at 4° C., and the polyester fabric 12 was carried by a moving belt that for a portion of its circuit was immersed in water. The dope solution was deposited onto the moving reinforcing polyester fabric 12 behind a doctoring blade. As the fabric traveled under the doctoring blade, a thin film of dope solution was formed on the reinforcing fabric. The position of the doctoring blade was adjusted to form a polysulfone layer approximately 40 microns thick.

When the dope solution contacted the water, the polysulfone along with the MICROBAN® Additive B precipitated onto the reinforcing polyester fabric to form a microporous polysulfone membrane 14 that was approximately 40 microns thick. The polysulfone membrane 14 was then soaked with an amine solution. The soaked polysulfone membrane 14 was placed on a moving belt in a kerosene bath comprising an organic peroxide catalyst, t-butylhydroperoxide, forming polyamide 16 having a thickness of about 0.2 micron on the outer surface of the polysulfone membrane 14. The resulting composite polyamide membrane 10 having a 120 micron reinforcing polyester fabric, a 40 micron layer of polysulfone and a 0.2 micron layer of polyamide was then tested.

During the test, the polysulfone membrane was extracted with methanol and analyzed for MICROBAN® Additive B. Gas chromatography confirmed the presence of about 2,700 ppm MICROBAN® Additive B in the composite membrane based on the weight of the polysulfone and the polyester composite. If only the polysulfone layer is considered, the concentration of MICROBAN® Additive B was about 8,100 ppm. These results indicated that the antimicrobial agent was incorporated into the polymeric material of the membrane and retained therein.

The composite membrane 10 was also tested using a AATCC-147 test method to determine its antibacterial characteristics. The testing showed that the composite membrane exhibits a 10 mm zone of inhibition for *S. aureus* and a 1 mm zone of inhibition for *K. pneumoniae*. These results indicate a good antimicrobial efficacy for the composite membrane.

The composite polyamide membrane 10 was then incorporated into a reverse osmosis module similar to that shown in FIG. 1 and tested. The influent and the permeate were monitored for the presence of bacteria. Normally, in an untreated reverse osmosis membrane, heterotrophic bacteria can be detected in the permeate within 72 hours. The composite polyamide membrane was tested for over a 3 month period without detecting any significant amount of bacteria in the permeate. When the module was disassembled, no discoloration of the membrane undersurface, which is indicative of bacterial growth, was observed. The salt rejection of the composite polyamide membrane 10 was greater than 99% for brackish water. In contrast, a control composite polyamide membrane that was not treated with MICROBAN® Additive B was badly discolored and showed a presence of bacteria within 72 hours.

Example 3

The use of polysulfone as the primary constituent for a substantially planar semi-permeable membrane as described in Example 2, is also applicable to filter modules incorporating hollow, thin polymer fibers that preferably comprise polysulfone and polyvinylidene fluoride and that incorporate an antimicrobial agent therein.

Three dope solutions of polyvinylidene fluoride, commercially available as Kynar Grade 460 and marketed by Elf Atochem North America, were prepared as follows:

|  | Dope Solution I | Dope Solution II | Dope Solution III |
| --- | --- | --- | --- |
| 1) Polyvinylidene fluoride | 16% | 16% | 16% |
| 2) Polyvinyl pyrrollidone | 4% | 4% | 4% |
| 3) Zinc Chloride | 4% | 4% | 4% |
| 4) Microban Additive B | 1.9% | 0.96% | 0.48% |
| 5) N-methyl pyrrollidone solvent | 74.1% | 75% | 75% |

Figure 6:
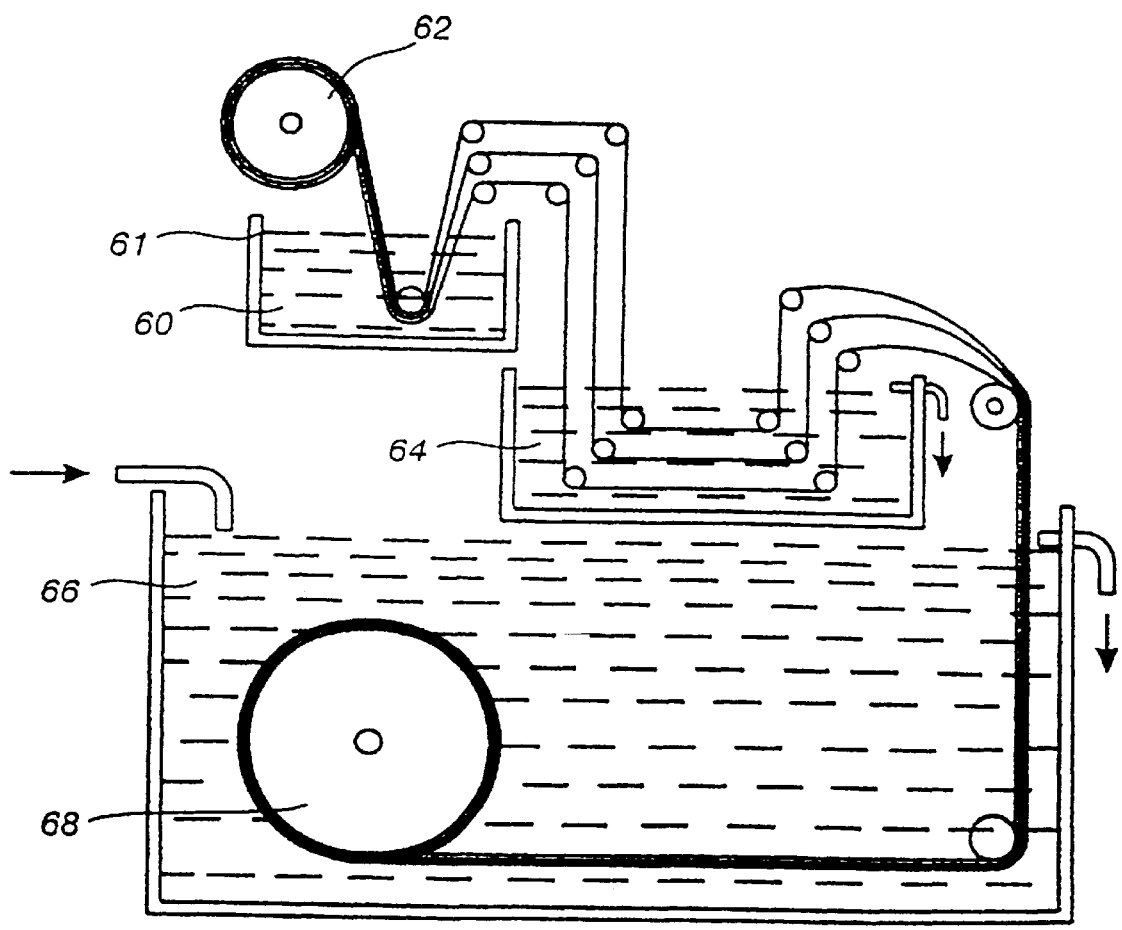
FIG. 6 is a schematic diagram of an apparatus used in the production of hollow fiber membrane in accordance with the present invention.

A polyester support tube woven from polyester filament fiber into a continuous tube was used to make this fiber. The inside diameter of the polyester tube was about 1.6 mm. FIG. 6 is a schematic diagram of a polyester tube 62 that is dipped into a vessel 61 containing one of the dope solutions (I, II, or 111) 60 described above. The viscosity of the dope solution was between about 25,000 to 35,000 centipoise. As the polyester support tube 62 is dipped into the vessel 61, the polyester support tube 62 picks up a film of dope solution. The support tube 62 is subsequently dipped into a water bath 64 maintained at about 40° C., where precipitation occurs. The formed hollow fiber is collected onto a spool 68, which in turn is allowed to remain in a second water bath 66 while the solvent is removed over a period of 2 days.

The produced polyvinylidene fluoride hollow fibers were subjected to microbiological test using a Kirby Bauer Test, the results of which are shown below in Table 3.

TABLE 3

| | Results (Zone Size) | |
| --- | --- | --- |
| Sample Identification | *S. aureus* | *E. coli* |
| 7196 - (1.92 Microban in dope) | 19 mm | 12 mm |
| 7197 - (0.98 Microban in dope) | 17 mm | 10 mm |
| 7198 - (0.48 Microban in dope) | 14 mm | 9 mm |

Figure 5:
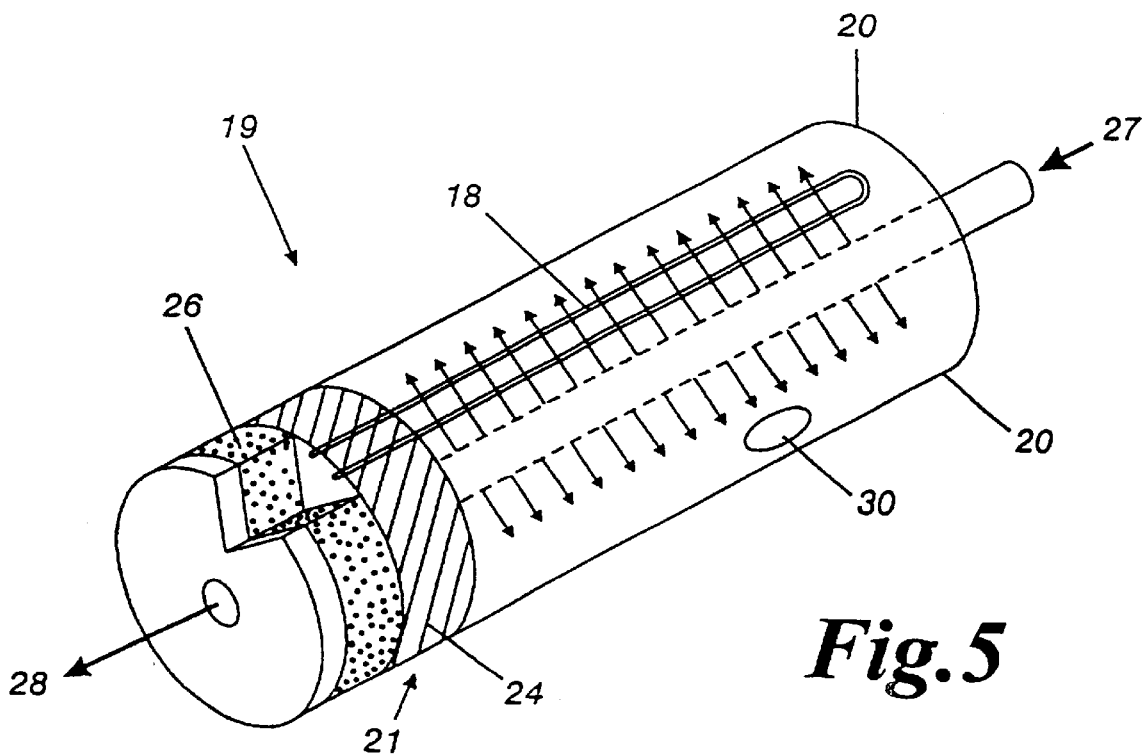
FIG. 5 is a schematic diagram of a hollow fiber microfiltration module in accordance with the present invention.

FIG. 5 is a schematic diagram of a hollow fiber reverse osmosis module in accordance with the present invention. The module 19 comprises a filter, shown generally at 21, incorporating a plurality of semi-permeable membranes in the form of thin hollow polymer fibers 18. The polymer fibers 18 are closed at one end and open at the other end. The polymer fibers 18 are bundled together and placed within a housing 20 that is sealed around the open ends of the polymer fibers in a manner to provide fluid communication between the open ends of the fiber 18 and the outside of the housing 20.

Water enters the housing 20 through feed inlet 27 and is forced through the semi-permeable walls of the hollow fibers 18, which reject dissolved contaminants. The permeate flows out of the open ends of the hollow fibers 18 which are secured in a layer of epoxy resin 24. The open ends of the hollow fibers 18 discharge the permeate into a porous disk 26 which collects and discharges permeate out of the housing 20 through a permeate outlet 28. The concentrate flows out of the housing 20 through a concentrate outlet 30. The filter 21 provides excellent contaminant rejection and flux due to the large surface area of the combined polymer fibers 18.

While the aforementioned examples are primarily directed toward the formation of semi-permeable membranes for reverse osmosis, the present invention is equally applicable to use in ultrafiltration and microfiltration processes.

Example 4

Microporous membranes using a polysulfone membrane were made in a manner similar to that described in Example 2. A dope solution of polysulfone, sold under the trade name "P 1700" by Union Carbide, was made using dimethyl formamide as a solvent. MICROBAN® Additive B was added to the dope solution at a level of 1%, 0.5% and 0.25% and the membranes were cast. The cast membranes were subsequently extracted in a Soxhlet Apparatus under overnight refluxing using methanol as solvent. Table 4 shows the results of the extract of the membranes indicating that MICROBAN® Additive B was retained in the cast polysulfone membranes. This is a qualitative test for the presence of antimicrobial agent and no attempt was made to extract the antimicrobial agent quantitatively by longer extraction times.

TABLE 4

| | |
| --- | --- |
| Sample: 1 - 1% Microban in dope solution | % extracted = .63% Microban |
| Sample: 2 - 0.25% Microban in dope solution | % extracted = .16% Microban |
| Sample: 3 - 0.5% Microban in dope solution | % extracted = .23% Microban |

SUMMARY OF THE ACHIEVEMENTS OF THE OBJECTS OF THE INVENTION

It is readily apparent that I have invented a cast semipermeable membrane having an antimicrobial agent incorporated therein which is especially useful a membrane filter that achieves a high level of separation of water soluble contaminants, resists fouling due to bacterial growth, inhibits the passage of bacteria to the downstream side of the membrane, and reduces downtime for water treatment processes.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. A membrane system comprising:
   at least one cast semi-permeable membrane comprising:
      a polymeric material having pore sizes suitable for reverse osmosis, ultrafiltration, nanofiltration, or microfiltration; and
      a non-leaching, non-metallic antimicrobial agent incorporated in said polymeric material and dispersed throughout the polymeric material of the membrane.

2. A membrane system in accordance with claim 1 wherein said polymeric material comprises a thin film of a cellulose acetate polymer.

3. A membrane system in accordance with claim 2 wherein said non-leaching antimicrobial agent is selected from the group consisting of 2,4,4'-trichloro-2'-hydroxy diphenol ether and 5-chloro-2-phenol (2,4-dichlorophenoxy).

4. A membrane system in accordance with claim 2 wherein said non-leaching antimicrobial agent is present in a concentration between about 100 ppm and 20,000 ppm by weight.

5. A membrane system in accordance with claim 1 wherein one of said at least one cast semi-permeable membrane is a thin film composite membrane.

6. A membrane system in accordance with claim 1 wherein said polymeric material is selected from the group consisting of polyolefins, polyester, aromatic polysulfones, polyphenylenesulfones, aromatic polyether sulfone, bisphenol, dichlorophenoxy sulfones, polyether ketones, sulfonated polyether ketones, phenoxides, polyvinylidene fluoride, nylon, vinyl chloride, polyacrilonitrile, polystyrene, and polytetrafluorethylene.

7. A membrane system in accordance with claim 6, wherein said layer of polymeric material is a microporous polysulfone material.

8. A membrane system in accordance with claim 1 wherein said polymeric material comprises a plurality of polymeric fibers surrounded by a housing, said plurality of polymeric fibers being generally cylindrical and having an outer wall and an inner wall thereby defining an annular space within each of said polymeric fibers, said annular space being in fluid communication with the outside of said housing.

9. A membrane system in accordance with claim 5 wherein said composite membrane comprises:
   a reinforcing fabric;
   a layer of said polymeric material; and
   a polyamide;
   wherein said layer of polymeric material is interposed between said reinforcing fabric and said polyamide.

10. A membrane system in accordance with claim 9 wherein said polymeric material is selected from the group consisting of polyolefins, polyester, aromatic polysulfones, polyphenylenesulfones, aromatic polyether sulfone, bisphenol, dichlorophenoxy sulfones, polyether ketones, sulfonated polyether ketones, phenoxides, polyvinylidene fluoride, nylon, vinyl chloride, polystyrene, and polytetrafluorethylene.

11. A membrane system in accordance with claim 9 wherein said reinforcing fabric comprises a material selected from the group consisting of polyolefins, polyester, aromatic polysulfones, polyphenylenesulfones, aromatic polyether sulfone, bisphenol A, dichlorodiphenoxysulfone, aromatic polyether ketones, sulfonated polyether ketones, phenoxides, polyvinylidene fluoride, polyacrilonitrile, nylon, vinyl chloride, polystyrene, polytetrafluorethylene, glass fiber, porous carbon, graphite, alumina based inorganic membranes, and zirconium oxide coated silica.

12. A membrane system in accordance with claim 11 wherein said non-leaching antimicrobial agent is selected from the group consisting of 2,4,4'-trichloro-2'-hydroxy diphenol ether and 5-chloro-2-phenol (2,4-dichlorophenoxy).

13. A membrane system in accordance with claim 9 wherein said non-leaching antimicrobial agent is further incorporated into said material of said reinforcing fabric.

14. A membrane system in accordance with claim 13 wherein said non-leaching antimicrobial agent is present in a concentration between about 100 ppm and 20,000 ppm by weight.

15. A membrane system in accordance with claim 13 wherein said polymeric fiber is selected from the group consisting of polysulfone, polyether sulfone, polyether ketone, polyvinylidene fluoride, sulfonated polyvinylidene fluoride, and polyacrilonitrile.

16. A membrane system in accordance with claim 13 wherein said non-leaching antimicrobial agent is selected from the group consisting of 2,4,4'-trichloro-2'-hydroxy diphenol ether and 5-chloro-2-phenol (2,4-dichlorophenoxy).

17. A membrane system in accordance with claim 13 wherein said non-leaching antimicrobial agent is present in a concentration between about 100 ppm and 20,000 ppm by weight.

* * * * *